(12) United States Patent
Xiong et al.

(10) Patent No.: US 9,000,927 B2
(45) Date of Patent: Apr. 7, 2015

(54) SYSTEM AND METHOD FOR MONITORING BIOMETRIC DATA

(71) Applicants: Sony Corporation, Tokyo (JP); Sony Network Entertainment International LLC, Los Angeles, CA (US)

(72) Inventors: True Xiong, San Diego, CA (US); Charles McCoy, Coronado, CA (US); Leo Pedlow, Ramona, CA (US)

(73) Assignees: Sony Corporation, Tokyo (JP); Sony Network Entertainment International LLC, Los Angeles, CA (US)

( * ) Notice: Subject to any disclaimer, the term of this patent is extended or adjusted under 35 U.S.C. 154(b) by 105 days.

(21) Appl. No.: 13/775,781

(22) Filed: Feb. 25, 2013

(65) Prior Publication Data

US 2014/0240130 A1    Aug. 28, 2014

(51) Int. Cl.
*G08B 23/00*   (2006.01)
*G05B 1/01*    (2006.01)
*G06Q 30/02*   (2012.01)

(52) U.S. Cl.
CPC .............. *G05B 1/01* (2013.01); *G06Q 30/0269* (2013.01)

(58) Field of Classification Search
None
See application file for complete search history.

(56) References Cited

U.S. PATENT DOCUMENTS

| | | | | |
|---|---|---|---|---|
| 2007/0100243 | A1* | 5/2007 | Lam et al. | 600/490 |
| 2009/0007596 | A1* | 1/2009 | Goldstein et al. | 63/1.11 |
| 2010/0265179 | A1* | 10/2010 | Ram | 345/163 |
| 2011/0121943 | A1* | 5/2011 | Morovitz et al. | 340/5.82 |
| 2011/0221622 | A1* | 9/2011 | West et al. | 341/176 |
| 2012/0249294 | A1* | 10/2012 | O'Connor | 340/5.53 |
| 2013/0060914 | A1* | 3/2013 | Callahan | 709/219 |
| 2013/0154811 | A1* | 6/2013 | Ferren et al. | 340/12.5 |

* cited by examiner

*Primary Examiner* — Travis Hunnings
(74) *Attorney, Agent, or Firm* — Frommer Lawrence & Haug LLP; William S. Frommer

(57) ABSTRACT

A method and system for monitoring biometric data. The method includes authenticating a user and providing content to a user device associated with the user. Biometric data associated with the user is obtained and compared to one or more threshold values. A representation of the comparison is generated and provided to the user.

19 Claims, 5 Drawing Sheets

SYSTEM AND METHOD FOR MONITORING BIOMETRIC DATA

BACKGROUND

1. Field of the Invention

This invention relates generally to passively periodically monitoring a user's biometric data. More particularly, the present invention relates to periodically measuring a user's biometric data using a remote controller or gaming device.

2. Background Discussion

Many victims of heart attacks and strokes are not aware of the symptoms until the condition has become serious. Conventional home-based monitoring typically involve sensors embedded in wearable devices, such as bracelets that obtain data about a patient.

SUMMARY

Embodiments of the present invention involve a system and method for monitoring and obtaining biometric data for a user. The system includes a device, such as an IPTV device, such as a remote control device or a gaming device that includes sensors to detect and transmit biometric data of the user.

Accordingly, one embodiment of the present invention is directed to a method and system for obtaining biometric data associated with a user that has been authenticated, comparing that biometric data to threshold values and generating data sets based on the comparison.

Another embodiment is directed to an apparatus and method as mentioned, wherein an alert condition is generated based on the data sets; and the alert condition is transmitted to a designated location.

Yet another embodiment is directed to an apparatus and method as mentioned, wherein content based on the data sets is provided to the user's device. For example, the content may be advertisement content; and the biometric data associated with the user is obtained while the advertisement content is being provided.

BRIEF DESCRIPTION OF THE DRAWINGS

To the accomplishment of the foregoing and related ends, certain illustrative embodiments of the invention are described herein in connection with the following description and the annexed drawings. These embodiments are indicative, however, of but a few of the various ways in which the principles of the invention may be employed and the present invention is intended to include all such aspects and their equivalents. Other advantages, embodiments and novel features of the invention may become apparent from the following description of the invention when considered in conjunction with the drawings. The following description, given by way of example, but not intended to limit the invention solely to the specific embodiments described, may best be understood in conjunction with the accompanying drawings, in which.

DETAILED DESCRIPTION

Figure 1:
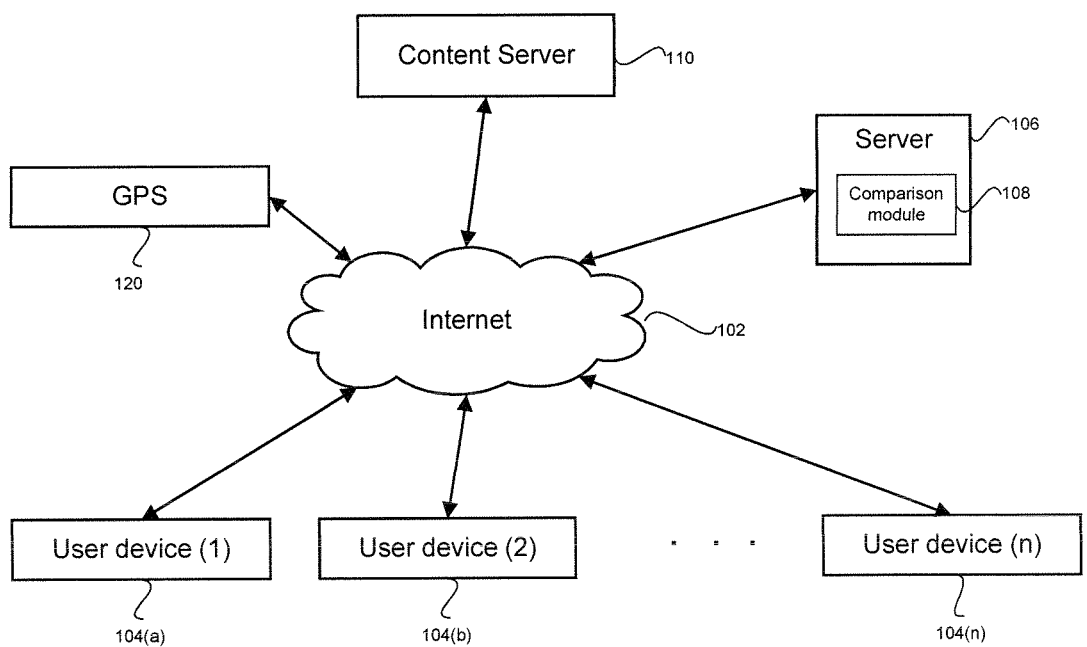
FIG. 1 shows a diagram of a network environment that supports embodiments of the present invention.

It is noted that in this disclosure and particularly in the claims and/or paragraphs, terms such as "comprises," "comprised," "comprising," and the like can have the meaning attributed to it in U.S. patent law; that is, they can mean "includes," "included," "including," "including, but not limited to" and the like, and allow for elements not explicitly recited. Terms such as "consisting essentially of" and "consists essentially of" have the meaning ascribed to them in U.S. patent law; that is, they allow for elements not explicitly recited, but exclude elements that are found in the prior art or that affect a basic or novel characteristic of the invention. These and other embodiments are disclosed or are apparent from and encompassed by, the following description. As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

Furthermore, the detailed description describes various embodiments of the present invention for illustration purposes and embodiments of the present invention include the methods described and may be implemented using one or more apparatus, such as processing apparatus coupled to electronic media. Embodiments of the present invention may be stored on an electronic media (electronic memory, RAM, ROM, EEPROM) or programmed as computer code (e.g., source code, object code or any suitable programming language) to be executed by one or more processors operating in conjunction with one or more electronic storage media. This electronic storage media may include, for example a non-transitory electronic storage medium/media such as a register, or other electronic repository or electronic storage location for data that is capable of storing data represented in electronic form, such as bits, bytes, kilobytes, waveforms, electronic signals, digital format and other data types, formats and forms of data.

Embodiments of the present invention may be implemented using one or more processing devices, or processing modules, or facilities. The processing devices, or modules, or facilities may be coupled such that portions of the processing and/or data manipulation may be performed at one or more processing devices and shared or transmitted between a plurality of processing devices, or modules, or facilities. A module, or unit or facility, as described herein may be a memory unit, or a memory unit operatively couple, either local or remote, to a processor, either dedicated or not-dedicated, such that the module, or unit or facility can either store and/or store and process data.

Indeed, the present invention may be implemented in a distributed or "cloud" computing environment in which shared resources, software and information are provided to computers and other devices over a network, which may be, for example, the Internet. "Cloud computing" typically involves delivering hosted services over the Internet. A cloud service typically has three distinct characteristics that differentiate it from traditional hosting. One characteristic is that it is sold on demand, typically by the minute or the hour; secondly, it is elastic—a user can have as much or as little of a service as they want at any given time; and thirdly, the service is usually fully managed by the provider (the consumer needs nothing but a personal computer and Internet access). Significant innovations in virtualization and distributed computing, as well as improved access to high-speed Internet have accelerated interest in cloud computing. The cloud can be private or public. A public cloud typically sells services to anyone on the Internet. (Currently, Amazon Web Services™ is the largest public cloud provider.) A private cloud is a proprietary network or a data center that supplies hosted services to a limited number of people. When a service provider uses public cloud resources to create their private cloud, the result is called a virtual private cloud. Private or public, the goal of cloud computing is to provide easy, scalable access to computing.

"Distributed computing", or "distributed systems" relate to a system of multiple autonomous computers or processing devices or facilities that communicate through a network. The computers interact with each other in order to achieve a particular goal. A computer program that runs in a distributed system is typically referred to as a "distributed program" and "distributed programming" is the process of writing such programs. Distributed computing also refers to the use of distributed systems to solve computational problems. Typically, in distributed computing, a problem is divided into multiple tasks, each of which is solved by one or more computers. In general, distributed computing is any computing that involves multiple computers remote from each other that each has a role in a computation problem or information processing.

FIG. 1 illustrates an example of a system 100 that supports embodiments of the present invention. The system 100 shown in FIG. 1 includes a network 102, one or more electronic user devices 104(a), 104(b) ... 104(n) (where "n" is any suitable number), a server module 106, a content server 110 and a GPS module 120.

The network 102 is, for example, any combination of linked computers, or processing devices, adapted to transfer and process data. The network 102 may be private Internet Protocol (IP) networks, as well as public IP networks, such as the Internet that can utilize World Wide Web (www) browsing functionality. An example of a wired network is a network that uses communication buses and MODEMS, or DSL lines, or a local area network (LAN) or a wide area network (WAN) to transmit and receive data between terminals. An example of a wireless network is a wireless LAN. Global System for Mobile Communication (GSM) is another example of a wireless network. The GSM network is divided into three major systems which are the switching system, the base station system, and the operation and support system (GSM). Also, IEEE 802.11 (Wi-Fi) is a commonly used wireless network in computer systems, which enables connection to the Internet or other machines that have Wi-Fi functionality. Wi-Fi networks broadcast radio waves that can be picked up by Wi-Fi receivers that are attached to different computers.

The electronic user devices, modules, or facilities, or units 104(a), 104(b) ... 104(n) (where "n" is any suitable number), (generally referred to as user device 104, herein) typically have biometric data acquisition capability, such as obtaining, recording, reproducing, transmitting and processing biometric data (such as blood pressure, pulse, retina and/or a combination of biometric data). The user device 104 is described in more detail in relation to FIG. 3 herein. The user device 104 may measure and monitor blood vessels in the eyes of the viewer. Also, the user device 104 can measure the intensity of a viewer's finger grips to measure a blood pressure level. The user devices 104 may be, for example, remote control devices, game control devices, or smartphone or any suitable device that can obtain and transmit data via a network (102). The user devices 104 may also be embodied as a Smartphone, IPTV (Internet Protocol Television) devices or other handheld device that can acquire and transmit biometric data. The user devices 104 may be electronic devices with processing capabilities and memory and an output displays, such as, laptop computers, desktop computers, cell phone, personal digital assistant (PDA), wireless handheld device, and the like. The user devices 104 may be capable of processing and storing and displaying data themselves or merely capable of obtaining data (i.e., both thin and fat terminals). The user devices 104 may be capable of displaying data. The user devices 104 are in bi-directional communication with network 102 as shown by the associated arrows. The bi-directional communication may be, for example, a serial bus such as IEEE 1394, or other wire or wireless transmission medium.

The server module, or facility, or unit, 106 is typically one or more processors with associated memory, such as computers, or other processing devices such as a desktop computer, laptop computer, personal digital assistant (PDA), wireless handheld device, cellular telephone, or the like. The server module 106 is capable of processing and storing data or merely capable of accessing processed and stored data from another location (i.e., both thin and fat terminals). The server 106 includes electronic storage locations, such as RAM, ROM, EEPROM, registers and any suitable electronic storage medium that can store electronic data. The storage functionality of server 106 may be used to store algorithms, such as the algorithms described herein. Storage may be any suitable electronic storage, such as RAM, ROM, EEPROM, or other storage medium, or cloud-based storage using local or remote storage via a network, such as storage at a remote server.

The server module 106 includes a comparison module 108. The comparison module 108 is used to process and compare biometric data received from the user devices 104. The comparison module 108 is used to store algorithms and data. The algorithms and data can be used to determine whether biometric data from a user exceeds a threshold. If so, an alert condition can be generated and provided to a user and/or emergency response provider.

The server module 106 is in bi-directional communication with network 102 as shown by the arrow. The bi-directional communication may be, for example, a serial bus such as IEEE 1394, or other wire or wireless transmission medium.

The content server 110 is a facility, or unit, that typically includes one or more processors with associated memory, such as computers, or other processing devices such as a desktop computer, laptop computer, personal digital assistant (PDA), wireless handheld device, cellular telephone, or the like. The content server module 110 is capable of processing and storing data or merely capable of accessing processed and stored data from another location (i.e., both thin and fat terminals). The content server module 110 is used to store electronic content, such as audio data, image data, which may include advertisement data, music data, and/or a combination thereof. The content server 110 may also access other storage databases, such as IMDB database as well as other electronic data. The content server 110 is in bi-directional communication with network 102 as shown by the associated arrow. The bi-directional communication may be, for example, a serial bus such as IEEE 1394, or other wire or wireless transmission medium.

The GPS module 120 is used to identify a location of user devices 104. The GPS module 120 is typically used to identify longitude and latitude coordinates of each user device 104. The GPS module can provide location data of each user device 104 to server 106. Server 106 can use the user device location data from GPS module 120 to correlate a user's location. The GPS module 120 is in bi-directional communication with network 102 as shown by the associated arrow. The bi-directional communication may be, for example, a serial bus such as IEEE 1394, or other wire or wireless transmission medium.

The user devices 104, server module 106, and content server 110 may be communication appliances, or user locations, or subscriber devices.

Embodiments of the present invention may be implemented using one or more processing devices, or processing modules. The processing devices, or modules, may be coupled such that portions of the processing and/or data manipulation may be performed at one or more processing devices and shared or transmitted between a plurality of processing devices.

The user devices 104 may be IPTV (Internet Protocol Television) devices, game controllers, television remote control devices, smart phones or other device capable of obtaining biometric data, such as blood pressure, retina scan, breathalyzer or a combination thereof and processing or reproducing or transmitting the acquired biometric data. The user devices 104 have memory and processing capabilities. Indeed, the user devices 104 may also access one or more computer readable storage media such as RAM-based storage (e.g., a chip implementing dynamic random access memory (DRAM)) or flash memory or disk-based-storage. Software code implementing present logic executable by the user device 104 may also be stored on one of the memories of the user device 104.

It is an embodiment of the present invention that the user devices 104 are IPTV devices. An IPTV device can access a vast pool of content provided by numerous content providers, such as provided by content server 110. The user device, as an IPTV device, may also be used to control further distribution of content that has been provided by a third party to the IPTV device so that unauthorized access is prevented. Typically, IPTV is controlled by a single input device and has a single display device.

Figure 2:
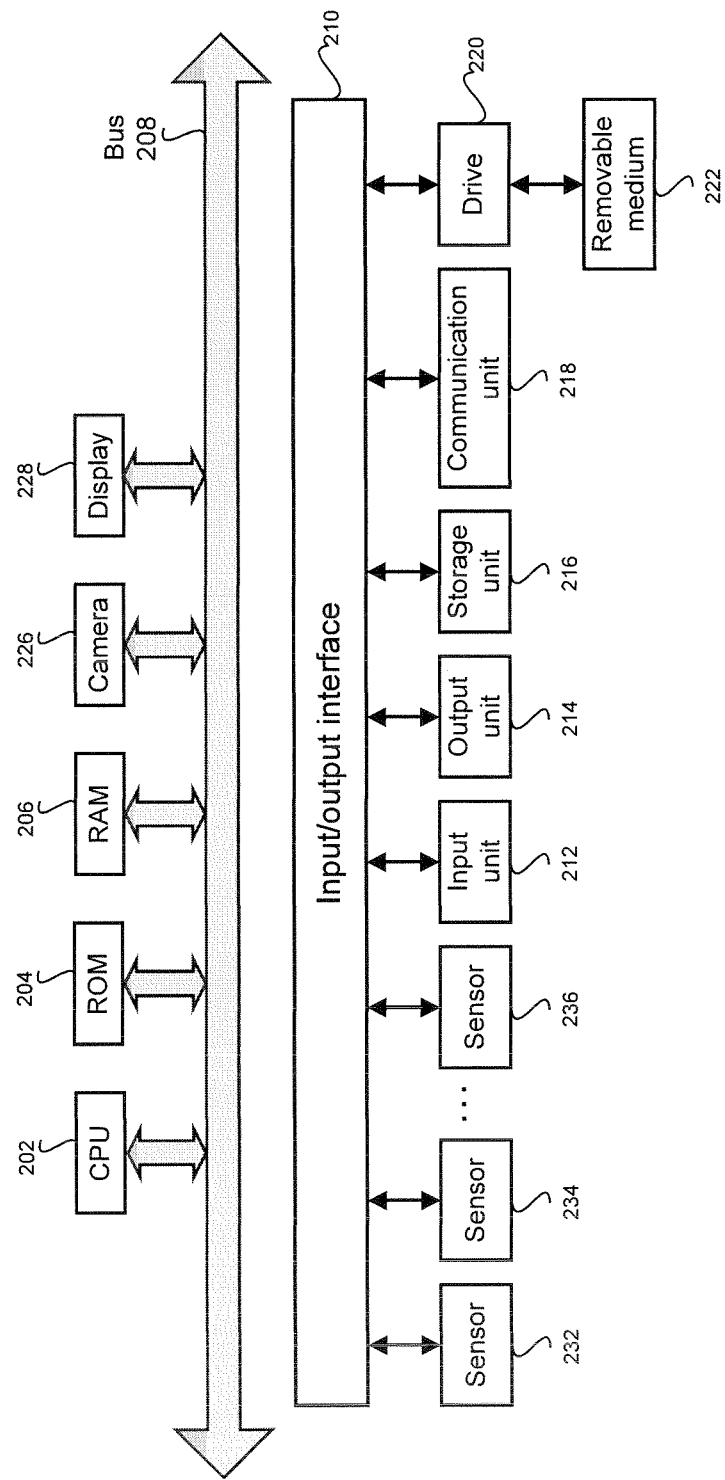
FIG. 2 shows diagram of modules and a network according to another embodiment of the present invention.

FIG. 2 illustrates an exemplary user device 104 according to an embodiment of the present invention. The exemplary user device 104 may be a remote controller, game control device, primary personal computer, a laptop, a tablet, a netbook, a cellular phone, smartphone, or a TV or other suitable device.

The exemplary user device 104 includes a CPU 202, a ROM 204, a RAM 206, a bus 208, an input/output interface 210, an input unit 212, an output unit 214, a storage unit 216, a communication unit 218, a drive 220, a removable medium 222, a camera 226, and a display 228. One or more sensors 232, 234 and 236 (while three sensors are shown, any suitable number of sensors may be used). The sensors 232, 234 and 236 are used to obtain biometric data from a user, such as retina scan, blood pressure and/or breathalyzer. These are also described in relation to the embodiment described in FIG. 3.

The CPU 202, the ROM 204, and the RAM 206 are interconnected to one another via the bus 208, and the input/output interface 210 is also connected to the bus 208. In addition to the bus 208, the input unit 212, the output unit 214, the storage unit 216, the communication unit 218, and the drive 220, sensors 232, 234 and 236 are connected to the input/output interface 210. The CPU 202 executes various kinds of processing in accordance with a program stored in the ROM 204 or in accordance with a program loaded into the RAM 206 from the storage unit 216 via the input/output interface 210 and the bus 208. The ROM 204 has stored therein a program to be executed by the CPU 202. The RAM 206 stores as appropriate a program to be executed by the CPU 202, and data necessary for the CPU 202 to execute various kinds of processing. The input unit 212 includes a keyboard, a mouse, a microphone, and the like. When the input unit 212 is operated by the user, the input unit 212 supplies an input signal based on the operation to the CPU 202 via the input/output interface 210 and the bus 208. The output unit 214 includes a display, such as a CRT (Cathode Ray Tube) or an LCD, a speaker, and the like. The storage unit 216 includes a hard disk, a flash memory, and the like, and stores a program executed by the CPU 202, data transmitted to the terminal 200 via a network, and the like. A removable medium 222 may be, for example a magnetic disk, an optical disc, a magneto-optical disc, or a semiconductor memory, which may be loaded as appropriate into the drive 220. The drive 220 reads data recorded on the removable medium 222 or records predetermined data on the removable medium 222. The camera 226 may take a still picture or a motion picture and store the taken picture to the user device. The display 228 may be part of the output unit 214 or may be a second display unit. The communication unit 218 includes a modem, a terminal adaptor, and other communication interfaces, and performs a communication process via the network of FIG. 1.

A user may store a plurality of contents on a display device, which enables the user to view the content, or may store contents in the "internet cloud," which allows a user to access the content anywhere as long as the network access is available. The user may choose to share the content stored in the user device or share the content stored in the "internet cloud." When the method and system of the present invention is implemented as software, the software may be installed in the user device. In another embodiment, the software may be provided by a server connected with the user device via a network (wired or wireless), which allows the user to user to execute the software through a web browser.

Figure 3:
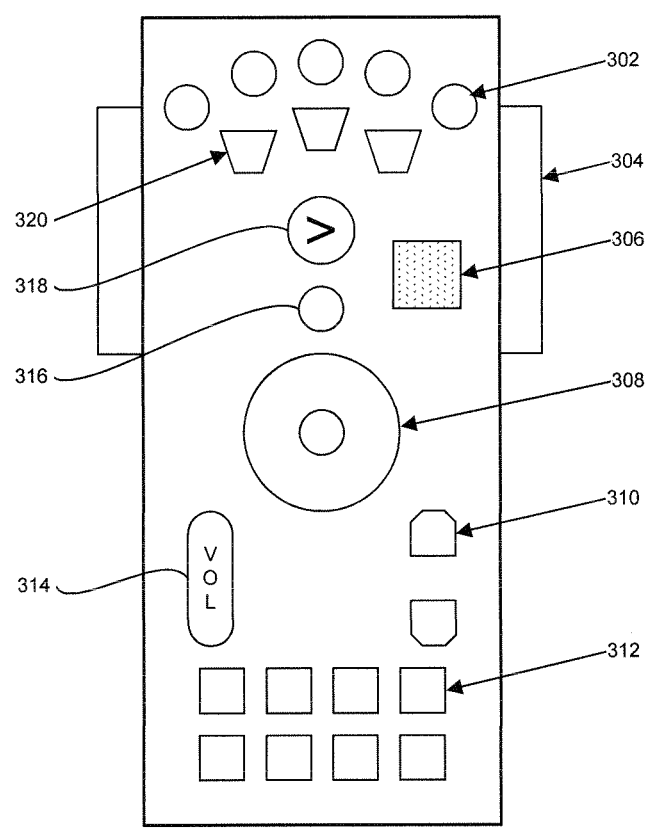
FIG. 3 shows an example of a user device according to an embodiment of the present invention.

FIG. 3 shows another example of a user device 300 according to an embodiment of the present invention. The user device 300 may be a control device for a display module, telephone, camera or combination thereof. The user device 300 has a plurality of input buttons, shown generally as 302. Function buttons 320, directional control button 318, retina scanner module 316, dial controller 308, volume control 314, channel selectors 310 and menu buttons 312, biometric sensor 304, and breathalyzer module 306.

Input buttons 302, function buttons 320, directional control button 318, dial controller 308, volume control 314, channel selectors 310 and number 312, which may be used to dial a telephone number. These input buttons are typically used for control of a display device, such as a television set, or game display module (e.g., display module 228 of FIG. 2) and/or telephone or camera. A user viewing content, such as a television show, video game, or other electronic content may use the control buttons of device 300 to control the display module.

Retina scanner module 316, biometric sensor module 304 and breathalyzer module 306 are used to obtain biometric data for a user.

Retina scanner 316 is a module that can be used to obtain retina data of a user using user device 300. The user's retina provides useful data related to the physiological condition of the user. For example, the retina data can be used to determine whether the user has been consuming alcohol, and the state of blood pressure in the eye. The retina scan data may also be used in conjunction with time data to determine how long a user has been viewing content and whether the length of time viewing the content is causing the user to suffer from eye strain. The biometric information obtained by sensor 316 may be obtained while a user is using the device 300 to play a video game or select content for viewing.

Biometric sensor module 304 is shown as disposed on an outer surface of the user device 300. The position is selected such that a user holding the device 300 may grasp the device 300 such that portions of the user's hand contact the sensor 304. Thus, the blood pressure of a user's finger tips may be obtained by sensor 304 and transmitted, for example via the network structure shown in FIG. 1. The biometric information obtained by sensor 304 may be obtained while a user is using the device 300 to play a video game or select content for viewing.

As shown in FIG. 3, portions of sensor 304 may be mounted on both sides of the device 300 to contact wrist and finger portions of either the right or left hand, depending on which hand the user is using to hold the device 300. Alternatively, the sensor 304 may be mounted or disposed at any suitable place to obtain the desired biometric user data.

Breathalyzer module 306 is used to obtain breath data from a user. If a user wishes to access certain features of a device, the user may be prompted to breath into sensor 306. The breath data may be transmitted to a remote location, via the network system shown in FIG. 1, and analyzed. If the breath data indicates that the user may have been drinking alcohol, the user may be prevented from accessing some functionality, such as email, or phone service. While breathalyzer module 306 is shown mounted on a top surface of device 300, the breathalyzer module 306 may be mounted at any suitable location. Alternatively, the breathalyzer module 306 may also be a discrete stand-alone device that is operatively coupled to a user device.

Figure 4:
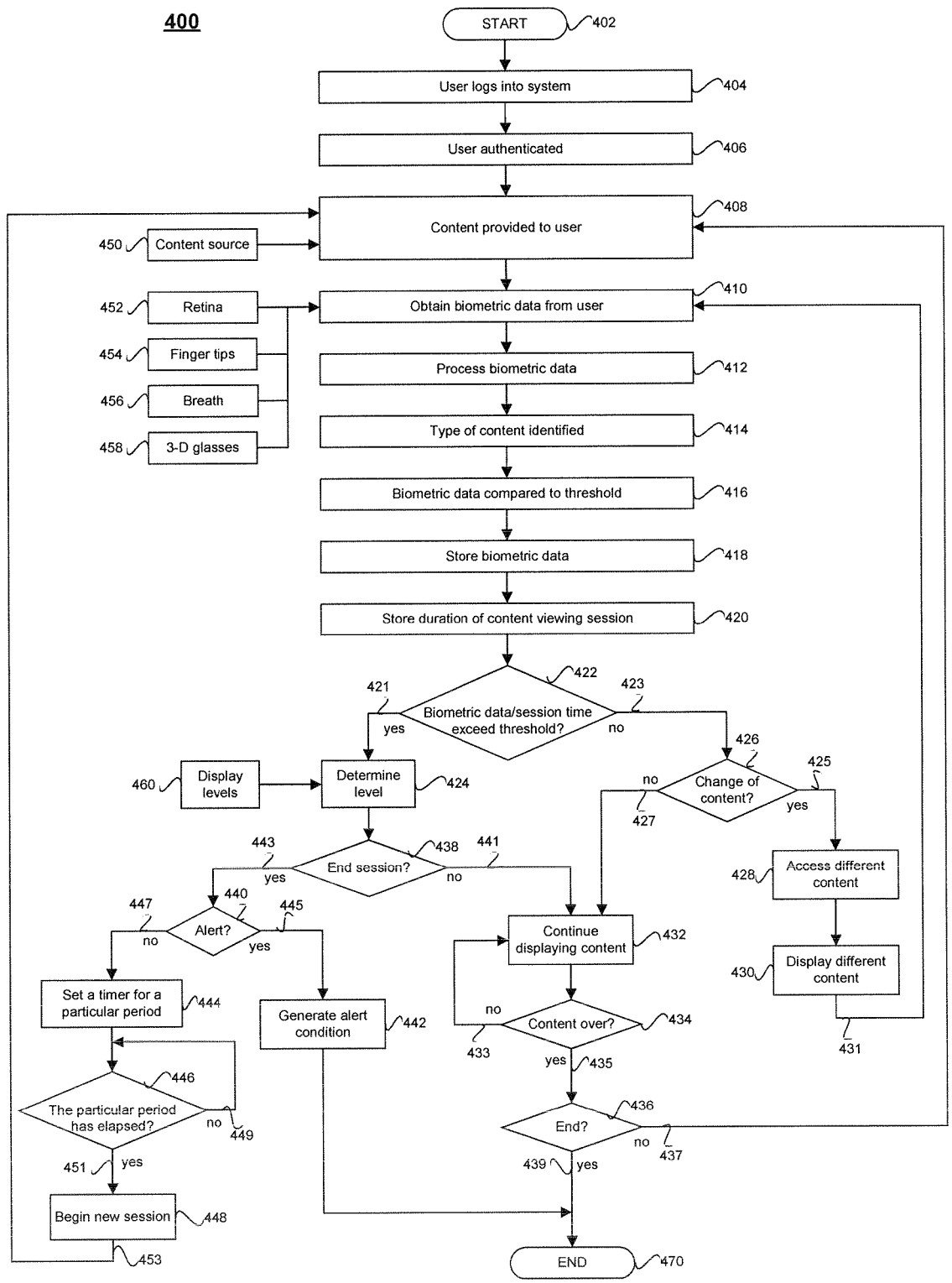
FIG. 4 shows a series of steps according to another embodiment of the present invention.

FIG. 4 shows a series of steps 400 according to another embodiment of the present invention. The series of steps 400 may be stored on a non-transitory computer readable medium or media (e.g., RAM, ROM, EEPRPOM, DRAM or other memory, electronic storage device or registry) and may be executed by a processor or plurality of processors. The storage medium may be resident on the user device or server module (as shown in FIG. 1 herein). The steps 400 are typically executed by a processor having adequate speed and processing capabilities. The execution may be at the user device and/or an associated server module and/or combination thereof. The steps 400 may be computer code or other program code (e.g., source code) that may be compiled into object code. The code, stored on a medium and/or accessed, is a module. The steps 400 may be stored on any one or more suitable modules described in relation to FIG. 1 and FIG. 2 herein.

The process 400 may be a subroutine that can be used in conjunction with another process or may be executed as a stand-alone process. Also, the process 400 may be used with the modules shown in FIGS. 1 and 2. The process 400 may be executed by a processor and begins, as shown by start step 402. A user logs into the system, as shown in step 402. The log in process may identify a user account for a device. Thus, more than one user may utilize a device with their individual account. The user is authenticated, as shown in step 406. The authentication process may include a user password or other identifying information to validate the user.

Content is provided to a user, as shown in step 408. This content may be audio, video, audio/video, video game content, music, image data or other electronic data that may be displayed on a display module or output via a speaker. The user may use a control device in conjunction with a display module or output module such that the control device orders or controls the output of the content on another module or device or facility. The content that is provided to a user may be obtained from one or more content source(s), as shown in step 450. These sources of content may include IMDB (Internet Movie Data Base) database, Internet content, and stored electronic content.

User biometric data is obtained, as shown in step 410. This biometric data may be, for example, retina data, blood pressure data, and/or breathalyzer data, or any combination thereof.

The obtained biometric data from a user may be processed, as shown in step 412. The processing typically occurs at a processing module, for example server module 106, as shown in FIG. 1. The processing may compare the obtained biometric data from a user to previously obtained biometric data for that user and/or standard data for the parameter, e.g., how long the user has been viewing the content, playing the video game, listening to the music. The source of the biometric data may be retina data (452), finger tip blood pressure reading (454), breathalyzer (456) and/or 3-D glasses (458) that obtain blood pressure data from a user's temple(s).

The type of content provided to the user is identified, as shown in step 414. This is used to determine whether a type of content accessed by a user, or provided to a user, causes an unhealthy rise in blood pressure, or other detectable condition.

The obtained biometric, which has been processed, may then be compared to threshold levels, as shown in step 416. This comparison may be between obtained data and stored user data that is used as a baseline. The threshold data may be obtained prior to a particular type of content being provided. For example, biometric data may be obtained when a user is logging into the system. That baseline data may then be compared to biometric data obtained while a viewer is playing a particular game or viewing particular content. A comparison between a user's biometric data may also be made based on whether the user is viewing advertisement data.

The biometric data obtained, including data related to content being viewed when the biometric data was obtained, may be stored, as shown in step 418. The biometric data and related data (i.e., type of content being viewed, duration of viewing session, and other related data) may be stored in a local memory and/or remote memory location, such as at a server module, as described herein. Indeed, the duration of a content viewing session is stored, as shown in step 420.

A determination may be made, as shown in step 422, whether the obtained biometric data and/or a session time of accessing (viewing and/or listening) content exceed a threshold. If so, "yes" line 421 shows that a level of excess is determined, as shown in step 424. The level of the biometric data and/or accessing time may be displayed on a display module or display unit, as shown in step 460.

A determination may be made whether to terminate or end the session, as shown in step 438. If so, "yes" line 443 shows that a determination is made whether to generate an alert condition, as shown in step 440. If so, "yes" line 445 shows that an alert condition is generated, as shown in step 442. The alert condition may be generated at a server module and transmitted to a hospital, emergency response station or other location to alert medical care providers of a distress situation that may require assistance.

In an embodiment in which an alert condition is not generated in step 440, "no" line 447 shows that a timer may be set for a period of time, as shown in step 444. This is to monitor a user's activity such that while an alert condition is not present, the session has ended for a certain period of time. A time cycle runs, as shown in step 446 such that following expiration of a time period, as shown by "yes" line 451, a new content session may begin, as shown in step 448. Line 453 shows that content providing step 408 is reached.

When a determination is made not to end the content session, "no" line 441 shows that the content is provided to a user, as shown in step 432. A determination is made whether the content is finished, as shown in step 434. If not, "no" line 433 returns to step 432. If the content is finished, "yes" line 435 reaches a determination step 436 to determine whether to end the user's accessing session. If so, "yes" line 439 leads to end step 470.

If the content session is not finished, "no" line 437 shows that content providing step 408 is reached.

In determination step 422, if the biometric data/session duration does not exceed a threshold, "no" line 423 shows that a determination to change the content is made, as shown in step 426. If the content is not changed, "no" line 427 shows that the content is continued to be displayed, as shown in step 432, described above.

If a determination is made to change the content, "yes" line 425 shows that different content is accessed, as shown in step 428. The different content is displayed/provided to a user, as shown in step 430. Line 431 shows that content providing step 408 is reached.

Figure 5:
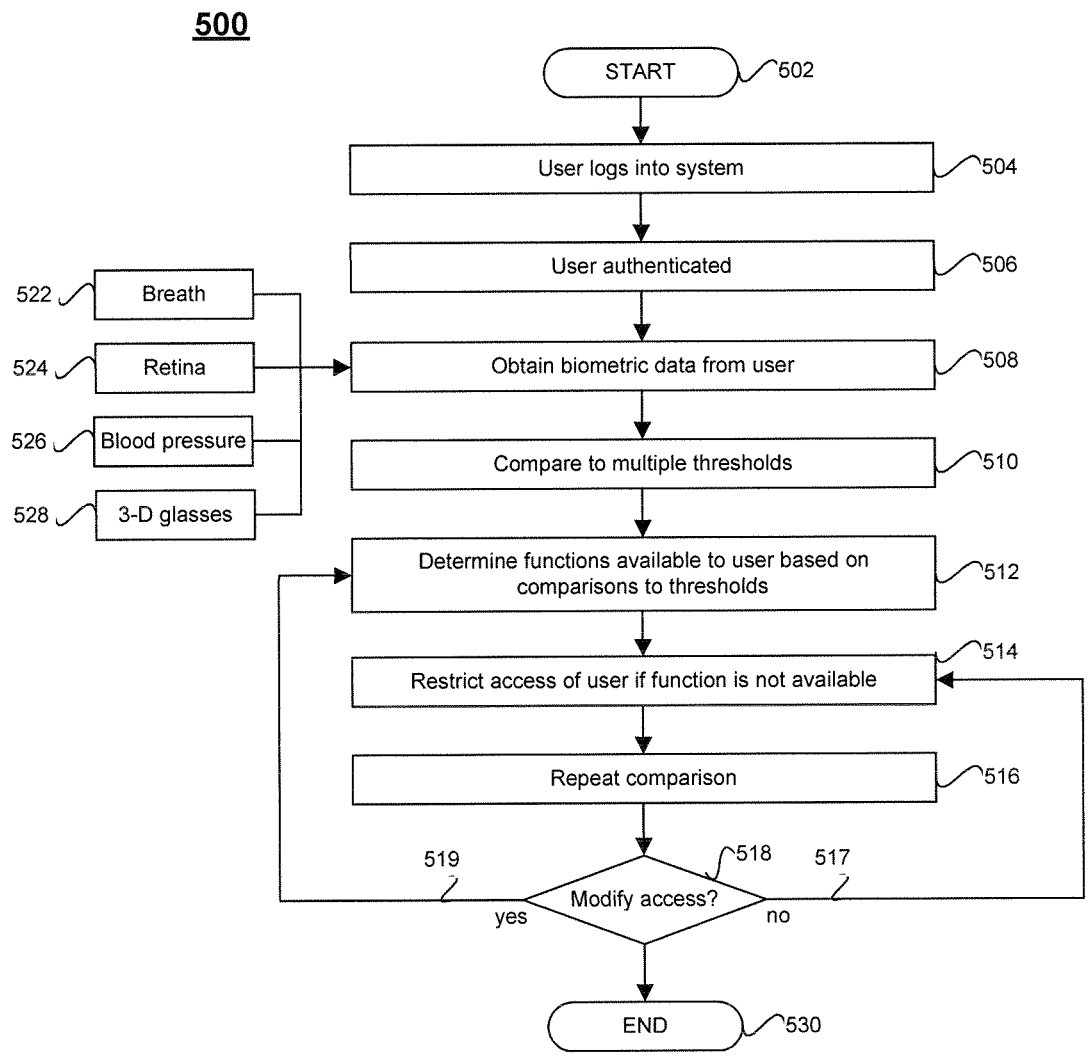
FIG. 5 shows a series of steps according to another embodiment of the present invention.

FIG. 5 shows a series of steps 500 according to another embodiment of the present invention. The series of steps 500 may be stored on a non-transitory computer readable medium or media (e.g., RAM, ROM, EEPRPOM, DRAM or other memory, electronic storage device or registry) and may be executed by a processor or plurality of processors. The storage medium may be resident on the user device or server module. The steps 500 are typically executed by a processor having adequate speed and processing capabilities. The execution may be at the client device and/or an associated server device, as described in relation to FIGS. 1 and 2 herein. The steps 500 may be computer code or other program code (e.g., source code) that may be compiled into object code. The code, stored on a medium and/or accessed, is a module. The steps 500 may be stored on any one or more suitable modules described in relation to FIG. 1 and FIG. 2 herein.

The process 500 may be a subroutine that can be used in conjunction with the process 400 in FIG. 4 or may be executed as a stand-alone process. Also, the process 500 may be used with the modules shown herein.

The process 500 may be executed by a processor and begins with start step 502. A user logs into the system, as shown in step 502. The log in process may identify a user account for a device. Thus, more than one user may utilize a device with their individual account. The user is authenticated, as shown in step 504. The authentication process may include a user password or other identifying information to validate the user.

User biometric data is obtained, as shown in step 508. This biometric data may be, for example, breathalyzer data (522) retina data (524), blood pressure data (526), and/or temple data from a sensor in eyeglasses or eyewear, such as 3-D glasses, or any combination thereof.

The obtained biometric data from a user may be processed and compared to multiple thresholds, as shown in step 510. The processing/comparison processes typically occurs at a processing module, for example server module 106, as shown in FIG. 1. The comparing process may compare the obtained biometric data from a user to previously obtained biometric data for that user and/or standard data for the parameter, e.g., how long the user has been viewing the content, playing the video game, listening to the music.

The comparison to threshold levels, may be between obtained data and stored user data that is used as a baseline. The threshold data may be obtained prior to a particular type of content being provided. For example, biometric data may be obtained when a user is logging into the system. That baseline data may then be compared to biometric data obtained while a viewer is playing a particular game or viewing particular content.

A determination of functions that are available for a user to access based on the comparison to thresholds is made, as shown in step 512.

The ability of a user to access functions is restricted, based on the comparison, as shown in step 514. For example, if the user's biometric data registers an elevated alcohol level, the user may be prevented from accessing email and/or telephone functionality. This reduces the likelihood that a user will send an email or make a telephone call when intoxicated.

The comparison, using updated biometric data may be repeated, as shown in step 516. Thus, if a person was prohibited from accessing some functionality, that prohibition may be removed based on updated biometric data.

A determination is made, as shown in step 518 whether to modify access to functions of a user device, based on the updated or repeated comparison. If so, "yes" line 519 shows that the step of determining functions available to a user (512) is reached. If not, "no" line 517 shows that access to certain functionality is denied the user. The process ends, as shown in step 530.

It will be appreciated from the above that the invention may be implemented as computer software, which may be supplied on a storage medium such as through a transmission medium such as a local-area network or a wide-area network, such as the Internet. It is to be further understood that, because some of the constituent system components and method steps depicted in the accompanying Figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A method for monitoring biometric data comprising:
   authenticating a user;
   providing content to a user device associated with the user;
   obtaining biometric data associated with the user;
   comparing the biometric data to one or more threshold values;
   generating one or more data sets based on the comparing step;
   selecting suitable content for a user based on the comparing step; and
   providing the selected suitable content to the user.

2. The method as claimed in claim 1, wherein the obtaining step further comprises: obtaining the biometric data at a specified periodic interval.

3. The method as claimed in claim 2, wherein the biometric data is retina data of a user.

4. The method as claimed in claim 2, wherein the biometric data is blood pressure data of a user.

5. The method as claimed in claim 2, wherein the biometric data is breathalyzer data of a user.

6. The method as claimed in claim 1, further comprising:
   generating an alert condition based on the data sets; and
   transmitting the alert condition to a designated location.

7. The method as claimed in claim 1, wherein the providing content step further comprises:
   identifying a particular genre of content to be provided to a user device based on the data sets.

8. The method as claimed in claim 1, further comprising:
   monitoring a period of time that content is being provided to a user device;
   comparing the period of time to a predetermined period of time; and
   terminating the provision of content based on the comparing step.

9. The method as claimed in claim 1, further comprising:
   generating a representation of the data sets; and
   providing the representation of the data sets to a user.

10. A method for monitoring biometric data comprising:
    authenticating a user;
    providing content to a user device associated with the user;
    obtaining biometric data associated with the user;
    accessing threshold data that provides a baseline;
    comparing the biometric data to one or more threshold values; and
    utilizing the threshold data to produce the one or more threshold values.

11. The method of claim 10, wherein the obtaining step further comprises: obtaining the biometric data at a specified periodic interval; and the biometric data is breathalyzer data of a user.

12. A method for monitoring biometric data comprising:
    authenticating a user;
    providing advertisement content to a user device associated with the user;
    obtaining user biometric data while the advertisement content is being provided to the user;
    comparing the biometric data to one or more threshold values; and
    generating one or more data sets based on the comparing step.

13. The method of claim 12, wherein the obtaining step further comprises: obtaining the biometric data at a specified periodic interval; and the biometric data is breathalyzer data of a user.

14. A method for permitting access to device functionality comprising:
    authenticating a user;
    storing baseline data representing a predetermined condition of the user obtaining biometric data associated with the user;
    comparing the biometric data to one or more threshold values, said threshold values being dependent upon said baseline data; and
    identifying device functionality that the user is permitted to access based on the comparing step.

15. The method as claimed in claim 14 further comprising:
    obtaining updated biometric data;
    performing a comparison between the updated biometric data and the one or more threshold values; and
    identifying device functionality that the user is permitted to access based on the comparison step using the updated biometric data.

16. A system for monitoring biometric data of a user comprising:
    a display to provide content to the user;
    a data store configured to store baseline data representing a predetermined condition of the user;
    at least one sensor to obtain biometric data associated with the user;
    a comparator coupled to said at least one sensor through a network and configured to compare the biometric data to one or more threshold values, said threshold values being dependent upon said baseline data; and
    a data set generator configured to generate one or more data sets based on the comparison.

17. The system as claimed in claim 16, wherein said data sets are alert conditions.

18. The system as claimed in claim 17, further comprising a transmitter coupled to said data set generator and configured to transmit said alert conditions to a designated location.

19. The system of claim 16, further comprising a source of content configured to transmit said content to said display dependent upon said comparison.

* * * * *